[12] United States Patent
Mulrooney et al.

(10) Patent No.: US 11,980,753 B2
(45) Date of Patent: May 14, 2024

(54) CATHETER FOR RECOVERY OF DYSPHAGIA

(71) Applicant: Phagenesis Limited, Manchester (GB)

(72) Inventors: Conor Mulrooney, Manchester (GB); Veronika Matei-Rascu, Manchester (GB)

(73) Assignee: Phagenesis Limited, Manchester (GB)

(*) Notice: Subject to any disclaimer, the term of this patent is extended or adjusted under 35 U.S.C. 154(b) by 1021 days.

(21) Appl. No.: 16/671,654

(22) Filed: Nov. 1, 2019

(65) Prior Publication Data
US 2020/0061370 A1    Feb. 27, 2020

Related U.S. Application Data

(63) Continuation of application No. 15/523,703, filed as application No. PCT/GB2015/053366 on Nov. 6, 2015, now abandoned.

(30) Foreign Application Priority Data

Nov. 6, 2014 (GB) .................................. 1419792

(51) Int. Cl.
| | | |
|---|---|---|
| A61N 1/05 | (2006.01) | |
| A61B 5/00 | (2006.01) | |
| A61B 5/03 | (2006.01) | |
| A61J 15/00 | (2006.01) | |
| A61L 29/04 | (2006.01) | |
| A61M 25/00 | (2006.01) | |
| A61M 39/10 | (2006.01) | |
| A61N 1/36 | (2006.01) | |

(52) U.S. Cl.
CPC ............ *A61N 1/0517* (2013.01); *A61B 5/037* (2013.01); *A61B 5/6852* (2013.01); *A61J 15/0003* (2013.01); *A61L 29/04* (2013.01); *A61L 29/041* (2013.01); *A61M 25/0009* (2013.01); *A61M 39/10* (2013.01); *A61N 1/0519* (2013.01); *A61N 1/36007* (2013.01); *A61N 1/3601* (2013.01)

(58) Field of Classification Search
CPC ........................ A61J 15/0003; A61M 25/0009
See application file for complete search history.

(56) References Cited

U.S. PATENT DOCUMENTS

| | | |
|---|---|---|
| 803,464 A | 10/1905 | Beck |
| 1,032,436 A | 7/1912 | Smith |
| 2,627,096 A | 2/1953 | Alessi |
| 2,779,985 A | 2/1957 | Turner et al. |

(Continued)

FOREIGN PATENT DOCUMENTS

| | | |
|---|---|---|
| CA | 2594296 A1 | 3/2006 |
| CN | 203389196 U | 1/2014 |

(Continued)

OTHER PUBLICATIONS

Bath et al., Pharyngeal electrical stimulation for neurogenic dysphagia following stroke, traumatic brain injury or other causes: Main results from the PHADER cohort study, EClinical Medicine 28 (2020) 100608, 9 pages.

(Continued)

*Primary Examiner* — Brandy S Lee
(74) *Attorney, Agent, or Firm* — Fortem IP LLP

(57) ABSTRACT

The present invention provides a catheter for assisting recovery from dysphagia.

7 Claims, 6 Drawing Sheets

(56) References Cited

U.S. PATENT DOCUMENTS

| | | | |
|---|---|---|---|
| 3,179,995 A | 4/1965 | Hawk | |
| 3,630,195 A | 12/1971 | Santomieri | |
| 3,839,841 A * | 10/1974 | Amplatz | A61M 25/0009 |
| | | | 53/425 |
| 3,894,706 A | 7/1975 | Mizusawa | |
| 3,951,136 A | 4/1976 | Wall | |
| 4,025,015 A | 5/1977 | Kolic | |
| 4,295,618 A | 10/1981 | Morota et al. | |
| 4,381,011 A | 4/1983 | Somers | |
| 4,453,545 A | 6/1984 | Inoue | |
| 4,531,937 A | 7/1985 | Yates | |
| 4,691,883 A | 9/1987 | Kurihara | |
| 4,707,906 A | 11/1987 | Posey | |
| 4,776,349 A | 10/1988 | Nashef et al. | |
| 4,840,337 A | 6/1989 | Zaugg | |
| 4,960,412 A | 10/1990 | Fink | |
| 5,109,870 A | 5/1992 | Silny et al. | |
| 5,125,904 A | 6/1992 | Lee | |
| 5,147,315 A | 9/1992 | Weber | |
| 5,179,952 A | 1/1993 | Buinevicius et al. | |
| 5,201,903 A | 4/1993 | Corbett et al. | |
| 5,372,131 A | 12/1994 | Heinen | |
| 5,382,239 A | 1/1995 | Orr et al. | |
| 5,389,074 A | 2/1995 | Parker et al. | |
| 5,457,852 A | 10/1995 | Liu | |
| 5,551,953 A | 9/1996 | Lattin et al. | |
| 5,588,424 A | 12/1996 | Insler et al. | |
| 5,755,225 A | 5/1998 | Hutson | |
| 5,759,490 A * | 6/1998 | Malchesky | A61L 2/04 |
| | | | 285/422 |
| 5,762,638 A | 6/1998 | Shikani et al. | |
| 5,800,402 A | 9/1998 | Bierman | |
| 5,836,895 A | 11/1998 | Ramsey | |
| 5,957,968 A | 9/1999 | Belden et al. | |
| 6,006,138 A | 12/1999 | Don | |
| 6,148,222 A | 11/2000 | Ramsey | |
| 6,259,938 B1 | 7/2001 | Zarychta et al. | |
| 6,266,548 B1 | 7/2001 | Lamade et al. | |
| 6,366,813 B1 | 4/2002 | Dilorenzo | |
| 6,464,697 B1 | 10/2002 | Edwards et al. | |
| 6,484,053 B2 | 11/2002 | Leelamanit et al. | |
| 6,611,699 B2 | 8/2003 | Krueger | |
| 6,613,025 B1 | 9/2003 | Palasis | |
| 6,658,294 B1 | 12/2003 | Zadeh et al. | |
| 6,804,866 B2 | 10/2004 | Lemke et al. | |
| 6,856,822 B2 | 2/2005 | Larsson | |
| 7,324,851 B1 | 1/2008 | Dilorenzo | |
| 7,598,839 B1 | 10/2009 | Wedley | |
| 7,871,430 B2 | 1/2011 | Pavcnik et al. | |
| 7,918,828 B2 | 4/2011 | Lundgaard et al. | |
| 8,048,062 B2 | 11/2011 | Adams et al. | |
| 8,092,433 B2 | 1/2012 | Hamdy | |
| 8,876,798 B2 | 11/2014 | Clark et al. | |
| 8,968,331 B1 | 3/2015 | Sochor | |
| 9,895,486 B1 | 2/2018 | Carey-Hench | |
| 9,982,742 B2 | 5/2018 | Loewe et al. | |
| 10,028,885 B2 | 7/2018 | Martin et al. | |
| 10,285,341 B2 | 5/2019 | McCaslin et al. | |
| 10,743,810 B2 | 8/2020 | Mulrooney | |
| 10,888,690 B2 | 1/2021 | Mulrooney | |
| 2001/0039413 A1 | 11/2001 | Bowe | |
| 2001/0054425 A1 | 12/2001 | Bertram | |
| 2002/0032468 A1 | 3/2002 | Hill et al. | |
| 2002/0065544 A1 | 5/2002 | Smits | |
| 2002/0165537 A1 | 11/2002 | Kelley et al. | |
| 2002/0177765 A1 | 11/2002 | Bowe et al. | |
| 2003/0036794 A1 | 2/2003 | Ragheb et al. | |
| 2004/0034396 A1 | 2/2004 | Asmar et al. | |
| 2004/0220645 A1 | 11/2004 | Kretschmer et al. | |
| 2004/0230162 A1 | 11/2004 | Tan | |
| 2005/0098688 A1 | 5/2005 | Miarka et al. | |
| 2005/0137459 A1 | 6/2005 | Chin et al. | |
| 2005/0146676 A1 | 7/2005 | Silvestro | |
| 2005/0192559 A1 | 9/2005 | Michels et al. | |
| 2005/0229933 A1 | 10/2005 | McGrail et al. | |
| 2006/0085049 A1 | 4/2006 | Cory et al. | |
| 2007/0074728 A1 | 4/2007 | Rea | |
| 2007/0089898 A1 | 4/2007 | Potter | |
| 2007/0156041 A1 | 7/2007 | Rea | |
| 2008/0009810 A1 | 1/2008 | Hamdy | |
| 2008/0147013 A1 | 6/2008 | Breton et al. | |
| 2008/0249507 A1 | 10/2008 | Hadani | |
| 2008/0255441 A1 | 10/2008 | Hadani | |
| 2008/0300530 A1 | 12/2008 | Massengale | |
| 2009/0062772 A1 | 3/2009 | Wakeford et al. | |
| 2009/0223698 A1 | 9/2009 | Gilliland et al. | |
| 2009/0275825 A1 | 11/2009 | Thomas | |
| 2009/0276025 A1 | 11/2009 | Burnes et al. | |
| 2010/0115739 A1 | 5/2010 | Mathur | |
| 2010/0170066 A1 | 7/2010 | Honeycutt | |
| 2010/0174170 A1 | 7/2010 | Razavi | |
| 2010/0206453 A1 | 8/2010 | Leeflang et al. | |
| 2010/0218975 A1 | 9/2010 | Mehan | |
| 2010/0317956 A1 | 12/2010 | Kartush | |
| 2011/0137374 A1 | 6/2011 | Kieval et al. | |
| 2011/0210215 A1 | 9/2011 | Nitsche et al. | |
| 2011/0251519 A1 | 10/2011 | Romoscanu | |
| 2012/0065469 A1 | 3/2012 | Allyn et al. | |
| 2012/0203058 A1 | 8/2012 | Kanapkey et al. | |
| 2012/0259208 A1 | 10/2012 | Bloom et al. | |
| 2012/0260921 A1 | 10/2012 | Sangwan | |
| 2013/0006323 A1 | 1/2013 | Tal et al. | |
| 2013/0197321 A1 | 8/2013 | Wilson | |
| 2013/0282078 A1 | 10/2013 | Wacnik | |
| 2014/0012235 A1 | 1/2014 | Pinchuk et al. | |
| 2014/0128936 A1 | 5/2014 | Laufer et al. | |
| 2014/0276663 A1 | 9/2014 | Pinchuk et al. | |
| 2014/0288384 A1 | 9/2014 | Mulrooney | |
| 2014/0303617 A1 | 10/2014 | Shimada | |
| 2014/0378941 A1 | 12/2014 | Su et al. | |
| 2015/0224280 A1 | 8/2015 | Pinchuk et al. | |
| 2017/0050014 A1 | 2/2017 | Rizik | |
| 2017/0224986 A1 | 8/2017 | Imran et al. | |
| 2017/0312497 A1 | 11/2017 | Mulrooney et al. | |
| 2018/0214672 A1 | 8/2018 | Mulrooney | |
| 2018/0235533 A1 | 8/2018 | Mulrooney | |
| 2019/0038894 A1 | 2/2019 | Bassi et al. | |
| 2019/0134380 A1 | 5/2019 | Mulrooney | |
| 2019/0134389 A1 | 5/2019 | Mulrooney | |
| 2020/0061369 A1 | 2/2020 | Mulrooney et al. | |
| 2020/0179045 A1 | 6/2020 | Levin et al. | |
| 2020/0330025 A1 | 10/2020 | Mulrooney | |
| 2021/0077784 A1 | 3/2021 | Mulrooney | |
| 2021/0077808 A1 | 3/2021 | Mulrooney et al. | |
| 2022/0160537 A1 | 5/2022 | Mulrooney | |
| 2022/0161029 A1 | 5/2022 | Mulrooney | |
| 2022/0161030 A1 | 5/2022 | Mulrooney | |
| 2022/0313981 A1 | 10/2022 | Mulrooney | |
| 2023/0181023 A1 | 6/2023 | Mulrooney | |
| 2023/0302244 A1 | 9/2023 | Mulrooney | |

FOREIGN PATENT DOCUMENTS

| | | |
|---|---|---|
| CN | 203954394 U | 11/2014 |
| CN | 204319485 U | 5/2015 |
| EP | 0510857 A1 | 10/1992 |
| EP | 0571514 A1 | 12/1993 |
| EP | 1179307 A2 | 2/2002 |
| EP | 2253350 A1 | 11/2010 |
| EP | 2693968 A1 | 2/2014 |
| EP | 3331597 A1 | 6/2018 |
| GB | 2169206 A | 7/1986 |
| GB | 2254253 A | 10/1992 |
| GB | 2294642 A | 5/1996 |
| GB | 2313316 A | 11/1997 |
| GB | 2532044 A | 5/2016 |
| GB | 2541039 A | 2/2017 |
| JP | S63200771 A | 8/1988 |
| JP | H05115563 A | 5/1993 |
| JP | H07500523 A | 1/1995 |
| JP | H08505291 A | 6/1996 |
| JP | H10118190 A | 5/1998 |
| JP | 2005312969 A | 11/2005 |
| JP | 2012512722 A | 6/2012 |

(56) References Cited

FOREIGN PATENT DOCUMENTS

| | | | |
|---|---|---|---|
| JP | 2014068716 A | 4/2014 | |
| WO | 9400050 A1 | 1/1994 | |
| WO | 9405361 A1 | 3/1994 | |
| WO | 9526777 A1 | 10/1995 | |
| WO | 9715349 A1 | 5/1997 | |
| WO | 9719667 A1 | 6/1997 | |
| WO | 03026741 A1 | 4/2003 | |
| WO | 2005051472 A2 | 6/2005 | |
| WO | 2006024825 A1 | 3/2006 | |
| WO | 2007129002 A1 | 11/2007 | |
| WO | 2009154718 A1 | 12/2009 | |
| WO | 2010023579 A1 | 3/2010 | |
| WO | 2010071812 A1 | 5/2010 | |
| WO | 2010091440 A2 | 8/2010 | |
| WO | 2012131303 A1 | 10/2012 | |
| WO | WO-2012131303 A1 * | 10/2012 | ......... A61B 18/1492 |
| WO | 2013109835 A1 | 7/2013 | |
| WO | 2014152808 A1 | 9/2014 | |
| WO | 2015027094 A1 | 2/2015 | |

OTHER PUBLICATIONS

Bath et al., Pharyngeal Electrical Stimulation for Treatment of Dysphagia in Subacute Stroke A Randomized Controlled Trial, Stroke, Jun. 2016, vol. 47, Issue 6, pp. 1562-1570.

Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.

Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.

Essa et al., The BDNF polymorphism VAL66Met may be predictive of swallowing improvement post pharyngeal electrical stimulation in dysphagic stroke patients, Neurogastroenterol Motil, 2017; 27, 7 pages.

Fraser et al., Differential changes in human pharyngoesophageal motor excitability induced by swallowing, pharyngeal stimulation, and anesthesia, Am J Physiol Gastrointest Liver Physiol, 285: G-137-G144, 2003.

Hamdy et al., The cortical topography of human swallowing musculature in health and disease, Nature Medicine, vol. 2, No. 11, Nov. 1996, pp. 1217-1224.

Hamdy, et al., Long-term reorganization of human motor cortex driven by short-term sensory stimulation, Nature Neuroscience, vol. 1, No. 1, May 1998, pp. 64-68.

Jayasekeran et al., Adjunctive Functional Pharyngeal Electrical Stimulation Reverses Swallowing Disability After Brain Lesions, Gastroenterology, 2010; vol. 138, No. 5, pp. 1737-1746.

Koestenberger, et al., A Pilot Study of Pharyngeal Electrical Stimulation of Orally Intubated ICU Patients with Dysphagia, Neurocrit Care (2020) 32: 532-538.

Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].

Magara, et al., Exploring the effects of synchronous pharyngeal electrical stimulation with swallowing carbonated water on cortical excitability in the human pharyngeal motor system, Neurogastroenterol Motil (2016), 11 pages.

Restivo et al., Pharyngeal electrical stimulation device for the treatment of neurogenic dysphagia: technology update, Medical Devices: Evidence and Research, 2018: 11, pp. 21-26.

Restivo et al., Pharyngeal Electrical Stimulation for Dysphagia Associated with Multiple Sclerosis: A Pilot Study, Brain Stimulation 6, 2013, pp. 418-423.

Sasegbon et al., Advances in the Use of Neuromodulation for Neurogenic Dysphagia: . . . , American Journal of Speech-Language Pathology, Jul. 2020, vol. 29, pp. 1044-1064.

Scutt, et al., Pharyngeal Electrical Stimulation for Treatment of Poststroke Dysphagia: Individual Patient Data Meta-Analysis of Randomised Controlled Trials, Stroke Research and Treatment, 2015, 8 pages.

Suntrup et al., Electrical pharyngeal stimulation for dysphagia treatment in tracheotomized stroke patients: a randomized controlled trial, Intensive Care Med (2015) 41: 1629-1637.

Suntrup-Krueger et al., Electrical pharyngeal stimulation increases substance P level in saliva, Neurogastroenterol Motil (2016) 28, pp. 855-860.

Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.

Gow, David , et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.

Hamdy, S. , et al., "Modulation of human swallowing behaviour by thermal and chemical stimulation in health and after brain injury", Neurogastroenterol Motil, vol. 15, No. 1, Feb. 2003, pp. 69-77.

Hamdy, Shaheen , et al., "Recovery of Swallowing After Dysphagic Stroke Relates to Functional Reorganization in the Intact Motor Cortex", Gastroenterology, vol. 115, No. 5, Nov. 1998, pp. 1104-1112.

Jasper, Herbert H., "The Ten Twenty Electrode System of the International Federation", Clinical Neurophysiol, vol. 10, pp. 370-375.

Kajii, Yuka , et al., "Sour taste stimulation facilitates reflex swallowing from the pharynx and larynx in the rat", Physiology & Behavior, vol. 77, No. 2-3, 2002, pp. 321-325.

Takeuchi, Hiro-Aki , et al., "Electrophysiological and Behavioral Studies of Taste Discrimination in the Axolotl (*Ambystoma mexicanum*)", Physiology & Behavior, vol. 56, No. 1, Jul. 1994, pp. 121-127.

Tutuian, R. , et al., "Effects of position on oesophageal function: studies using combined manometry and multichannel intraluminal impedance", Neurogastroenterol Motil., vol. 15, No. 1, Feb. 2003, pp. 63-67.

Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108,, 1998, pp. 1-16.

Fraser, Chris et al., Driving Plasticity in Human Adult Motor Cortex is Associated with Improved Motor Function After Brian Injury, Neuron, vol. 34, 831-840, May 30, 2002.

International Search Report and Written Opinion of PCT Application No. PCT/GB2015/053366 , dated Jan. 29, 2016, 15 pages.

International Search Report for Appl No. GB1419792.5 dated Jul. 23, 2015, 2 pages (Claims 16-27).

International Search Report for Appl No. GB1419792.5 dated Jul. 23, 2015, 3 pages (Claims 28-39).

International Search Report for Appl No. GB1419792.5 dated Jul. 23, 2015, 3 pages (Claims 50-51).

International Search Report for Appl No. GB1419792.5 dated Jul. 24, 2015, 3 pages (Claims 40-41).

International Search Report for Appl No. GB1419792.5 dated Jul. 24, 2015, 3 pages (Claims 42-49).

International Search Report for Application No. GB1419792.5 dated Apr. 22, 2015, 4 pages (Claims 1-15).

Wilmskoetter, Janina , et al., "Cortical and Subcortical Control of Swallowing—Can We Use Information From Lesion Locations to Improve Diagnosis and Treatment for Patients With Stroke?", American journal of speech-language pathology vol. 29,2S (2020): 1030-1043. (Year: 2020).

* cited by examiner

CATHETER FOR RECOVERY OF DYSPHAGIA

RELATED APPLICATIONS

This application is a continuation of U.S. patent application Ser. No. 15/523,703, filed May 2, 2017, which is a national phase application filed under 35 USC § 371 of PCT Application No. PCT/GB2015/053366 with an international filing date of Nov. 6, 2015, which claims priority to GB 1419792.5, filed Nov. 6, 2014. Each of these applications is herein incorporated by reference in their entirety for all purposes.

FIELD OF THE INVENTION

The present invention relates to a catheter particularly, although not exclusively, for facilitating recovery from dysphagia.

BACKGROUND OF THE INVENTION

Dysphagia is the condition whereby a patient has difficulty in swallowing, or is unable to swallow safely. Dysphagia may be caused, for example, by stroke, neurodegenerative diseases, brain tumours or, in some cases, by other co-morbidity, such as respiratory disorders.

Swallowing is a rigidly ordered sequence of events that results in the propulsion of food from the mouth through the pharynx and oesophagus to the stomach. At the same time, respiration is inhibited and food is prevented from entering into the trachea. Swallowing can be initiated voluntarily, but thereafter it is almost entirely under reflex control. The swallow reflex is typically initiated by sensory impulses from tactile receptors (particularly those located near the opening of the pharynx) being transmitted to certain areas in the medulla. The central integrating areas for swallowing lie in the medulla and lower pons; they are collectively called the swallowing centre. Motor impulses travel from the swallowing centre to the musculature of the pharynx and upper oesophagus via various cranial nerves. This lower swallowing centre in the brainstem is under regulatory control by higher centres in the cerebral cortex. These higher swallowing centres or regions control the voluntary initiation and modulation of the swallow.

Swallowing occurs in three stages. In the oral or voluntary phase, food is moved towards the back of the mouth by the tongue, and forced into the pharynx, where it stimulates the tactile receptors that initiate the swallowing reflex.

In the pharyngeal stage of swallowing, food passes through the pharynx by constriction of the walls of the pharynx, backward bending of the epiglottis, and an upward and forward movement of the larynx and trachea. During the pharyngeal stage, respiration is reflexively inhibited.

In the oesophageal stage of swallowing, food moves down the oesophagus and into the stomach, assisted by one or more peristaltic waves.

Although the main function of swallowing is the propulsion of food from the mouth into the stomach, swallowing also serves as a protective reflex for the upper respiratory tract, preventing unwanted particles from entering the tract. Food or liquid that enters into the airways may act as a locus for infection and this type of infection can be life threatening. For instance, dysphagia after a stroke can be a devastating problem, as it carries a six-fold increased risk of aspiration pneumonia.

International patent application no. PCT/GB2005/003289 describes a method for treating dysphagia with electrical stimulation of the pharynx. A catheter is insertable into the body of a patient for delivering nutrients to the stomach. Electrodes are positioned on an outer surface of the catheter such that when the electrodes are positioned to be in contact with the pharynx, electrical stimulation is applied.

International patent application no. WO2012/131303 describes a catheter for the treatment of dysphagia. The catheter comprises a feeding tube for delivering nutrients to a patient's stomach and a sleeve positioned around the catheter and movable relative to the catheter. Electrodes are positioned on an outer surface of the sleeve and can be moved into contact with the pharynx by adjusting the position of the sleeve relative to the feeding tube.

It is an aim of the present invention to provide improvements to the treatment of dysphagia through electrical stimulation of the pharynx. In particular it is an aim of the present invention to provide an improved catheter, and associated apparatus, for this purpose.

SUMMARY OF THE INVENTION

A first aspect of the invention provides a catheter for assisting recovery from dysphagia, the catheter comprising a feeding tube, a sleeve for receiving the feeding tube and being movable longitudinally relative to the feeding tube, and a retaining formation attached to the sleeve for fixing the position of the sleeve relative to the feeding tube, wherein the retaining formation comprises a first part and a second part connected by a living hinge, the second part being movable relative to the first part between an open position whereby the sleeve can be moved longitudinally relative to the feeding tube and a closed position whereby the feeding tube is clamped between the first part and the second part of the retaining formation to positionally fix the sleeve relative to the feeding tube.

In some medical applications, for example in the application of intraluminal electrical pharyngeal stimulation, the position of the sleeve within the patient is critical to the effective application of treatment. The present invention allows the sleeve to move relative to the feeding tube when required. Once the sleeve is in the desired position, the feeding tube is clamped to the sleeve to create the assembled catheter. This allows optimal relative positioning of both feeding and treatment functions of the assembled catheter outside of the patient. When subsequently inserted into the patient the feeding tube part of the catheter will be in the correct position for feeding (i.e., in the stomach) and the electrodes located on the outer surface of the sleeve will be in the correct position in the oropharynx for electrical stimulation. The entire catheter may then be fixed in position within the patient by taping to the patient's external anatomy for example, meaning that the position of both the sleeve and feeding tube functions are always located correctly.

The second part of the retaining formation may comprise a thermoplastic elastomer liner.

To facilitate ease of insertion into a patient, catheters are typically flexible. Application of a clamping force risks pinching the feeding tube and preventing fluid from passing therethrough. Use of a retaining formation with a thermoplastic elastomer liner inhibits longitudinal movement of the sleeve relative to the feeding tube by way of a combination of compressive force and friction provided by the compliant behaviour of the liner in contact with the feeding tube.

The catheter may comprise a connector for receiving a part of the sleeve and the connector may comprise a mounting element for receiving the retaining formation.

The mounting element may be part of a sliding interface between the connector and the retaining formation and may include a snap fit element co-operable with the connector.

The snap fit element may be part of the retaining formation and may be in the form of a resilient finger.

The retaining formation may further comprise a closure for releasably locking the first and second parts of the retaining formation together when in a closed condition.

The use of a closure, preferably a clasp, to lock the first and second parts of the retaining formation together provides a repeatable means of applying a known compressive force to a sleeve. This controlled compressive force in combination with the use of the high friction elastomeric liner provides the correct balance to prevent unwanted movement of the feeding tube relative to the sleeve, without restricting the passage of feed material via the internal lumen of the feeding tube. A second aspect of the invention provides a catheter for assisting recovery from dysphagia, the catheter comprising a feeding tube, a sleeve for receiving the feeding tube and being movable longitudinally relative to the feeding tube, and a seal located on the sleeve and acting upon the outer surface of the feeding tube, wherein the seal comprises a first end and a second end with a lumen extending therebetween, the first end of the seal receiving a proximal end of the sleeve and the second end of the seal receiving the feeding tube, wherein the lumen has an internal flange for acting on an outer surface of the feeding tube, the flange both inhibiting fluid from a patient being drawn up between the sleeve and the feeding tube, and, providing a means to the clean the surface of the feeding tube if said feeding tube is withdrawn from the patient.

In use, the feeding tube is normally left inserted into the patient for an extended period of time. In the event that during this extended period the feeding tube should become irretrievably blocked by material within its lumen, it is possible to open the closure of the retaining formation on the sleeve and withdraw the feeding tube from the patient whilst leaving the sleeve in place within the patient. Given that the feeding tube whilst located within the patient may become coated with biological and potentially infective material it is desirable that such material is not withdrawn during the process of removing the feeding tube. Provision of a seal that acts on the surface of the feeding tube allows this risk to be reduced. The blocked feeding tube can then be replaced with a new feeding tube by feeding it into the patient via the sleeve still in place within the patient.

In addition, when the sleeve is normally positioned on the feeding tube, a narrow gap is formed between the internal lumen of the sleeve and the external surface of the feeding tube. In use the terminal end of the sleeve will be located within the upper region of the oesophagus. It is possible that fluid from within the patient may be drawn up into that gap between the outer surface of the feeding tube and the inner surface of the sleeve by way of capillary action. Provision of a seal between the feeding tube and the seal reduces the risk of capillary action occurring.

A third aspect of the invention provides a catheter for assisting recovery from dysphagia, the catheter comprising a feeding tube, a sleeve, having a proximal end and a distal end, for receiving the feeding tube and being movable longitudinally relative to the feeding tube, wherein the sleeve is constructed from an inner layer and an outer layer, the inner layer being formed from a first material selected to have a first material characteristic and the outer layer being formed from a second material selected to have a second, different from the first, material characteristic.

Preferably, the first material characteristic is a low coefficient of friction and the second material characteristic is flexibility. Preferably, the second material extends further towards the distal end of the catheter than the first material.

The low coefficient of friction of the first material forming the inner layer of the sleeve facilitates the easy movement of the sleeve along the surface of the feeding tube when located outside the patient. It also facilitates, if required, the easy removal of the feeding tube from the sleeve even when the assembled catheter is located within the patient. Materials that provide the required low coefficient of friction (such as fluoropolymers) tend to be relatively stiff in nature and therefore make the sleeve stiffer than the feeding tube.

The first material may be fluorinated ethylene propylene (FEP) and the second material may be polyurethane.

Use of FEP is advantageous as FEP provides a very high dielectric strength and consequently a high resistance value. FEP is also very low friction which will allow for a feeding tube to move within the sleeve with little or no resistance. FEP is also optically transparent. This combination of features enables a multi-functional sleeve for use in a catheter to be produced.

The sleeve may have a position indicator which may be in the form of a printed window or ring, each window or ring signifying a characteristic of the patient.

Prior to insertion into a patient the relative position of the sleeve and feeding tube are adjusted based on anatomical measurements made on that patient to create the assembled catheter. This ensures that the assembled catheter once inserted as a fixed unit will have both feeding and stimulation functions optimally located for that specific patient.

The assembled catheter is inserted into the patient nasally and through the pharynx. The feeding tube part is further inserted into the oesophagus and its terminal end located in the stomach. The sleeve, located on the surface of the feeding tube and fixed in place, is co-inserted to the point where its distal end is located at least within the upper oesophageal sphincter (UOS) or below the UOS and in the upper oesophagus. The feeding tube and the outer layer of the sleeve are both formed from a highly flexible thermoplastic such as polyurethane in order to facilitate ease of insertion and minimise patient discomfort once in place.

During insertion of the assembled catheter, it must be passed through some internal anatomical curves, for example at the rear of the nasal cavity and in the transition from nasal cavity to nasopharynx. As the catheter bends to pass through the curves the terminal end of the sleeve does not bend as easily as the feeding tube due to the inflexible nature of the FEP inner layer. This can create a sharp edge that in contact with internal patient tissue could cause mechanical damage. This is addressed by the third aspect of the present invention whereby the sleeve has an additional section of material at its distal end forming an extended tip and comprising the same material as the outer layer of the sleeve.

The distal end of the extended tip may be tapered such that the wall of the tip is made thinner or the internal diameter reduced to form a smooth transition from the sleeve to the feeding tube.

The tapered tip not only prevents scraping of patient tissues but also provides enhanced comfort during insertion. An additional advantage of this flexible tip section is that it extends the sleeve into the UOS. This means that in the event that the feeding tube is withdrawn and replaced, the replacement feeding tube is directed correctly towards the oesophagus and thereafter the stomach, rather than towards the entrance to the airways. In effect, the sleeve and tip located within the UOS act as a guide for replacement feeding tube insertion. An additional advantage of the tapered distal end of the extended tip is that it reduces the risk of ingress of unwanted liquid biological material entering into the gap between the terminal end of the sleeve and the outer surface of the feeding tube.

The catheter of each of the first, second and third aspects of the invention may be inserted nasally into the body of a patient.

A fourth aspect of the invention provides a method of manufacturing a catheter comprising providing a pre-formed storage container having one or more formations for receiving at least part of a catheter, providing a catheter as claimed in accordance with the teachings described herein, inserting the catheter into the storage container such that at least part of the catheter is received and deformed by the one or more formations of the storage container, and exposing the storage container to pre-determined conditions of one or more of temperature, humidity, pressure, vacuum, gas or radiation for a pre-determined time, whereby upon completion of the application of those conditions, at least part of the catheter maintains its deformed shape when removed from the storage container.

A fifth aspect of the invention provides a catheter for assisting recovery from dysphagia comprising a tube having a lumen therethrough, wherein the tube comprises a first section having a first radius of curvature and a second section having a second radius of curvature.

Preferably the tube comprises at least one electrode for imparting electrical stimulation to a patient's tissue.

When a catheter is inserted into a patient it may have to navigate certain anatomical features before it is located in its final position. In addition it is desirable once in its final position that it causes minimal discomfort and does not give rise to tissue damage through the application of mechanical pressure or force. This is particularly important if the catheter must be in place for an extended period of time. If the shape of the catheter is such that it conforms more exactly to the general anatomical features of the insertion path or preferred final position then it may be more readily tolerated by the patient or may reduce the risk of tissue trauma. A pre-formed shape is also advantageous in that it the catheter is easy to fix in place and the at least one electrode makes good contact with the patient's tissue.

It is particularly advantageous if the storage container used to confer the shape to the catheter is the final packaging for the catheter. It is additionally particularly advantageous if the conditions that facilitate the change in shape are part of the manufacturing process for the catheter, for example terminal sterilisation of the catheter and packaging using EtO sterilisation providing the necessary conditions to configure the shape.

A sixth aspect of the invention provides an insulated wire comprising one or more strands, or cables, encapsulated by a first, second and third insulation, each of different materials.

Medical electrical devices require robust and effective electrical insulation to protect the patient and user from unintended electrical discharge. In order to meet regulatory guidelines, this insulation must be provided and arranged in a defined manner. The fifth aspect of the present invention provides a suitable insulation by providing three means of electrical insulation, two distinct types of insulation applied to a conductive wire and a third means provided by the physical environment into which this insulated wire is located.

The first insulation (an enamel layer) applied directly to the conducting wire may preferentially comprise a polymer film of polyamide/polyimide. This provides a first high dielectric coating that delivers insulation of 1500V or more with a thickness of less than 20 microns. The second layer is preferentially of parylene and is applied to the enamel layer. The nature of the deposition process for parylene means that it is non-destructive to the underlying enamel. This provides a second high dielectric coating delivering a further 1500V or more with an additional thickness of less than 15 microns.

The third insulation is provided by the environment into which the doubly insulated wire is located. The wire is inserted into a lumen located within the wall of the sleeve. The insulation is therefore provided either by the outer layer of the sleeve (polyurethane) or by the inner layer of the sleeve (FEP). Both of these layers are capable of providing a further 1500V or greater of electrical insulation. After insertion the lumens in the sleeve are closed by heating the sleeve to reflow the material. The reflowed material bonds to the second insulation which advantageously fixes the position of the wires within the sleeve.

In order to meet the requirements of the applicable regulatory standards three layers of insulation each of which provide 1500V or more must be present. Whilst many materials have the necessary dielectric strength to insulate to this level, provision of multiple independent layers with limited thickness in a fashion that is non-destructive to underlying layers is not obvious. The materials selected offer excellent insulation values and were selected after extensive testing of alternative materials.

A seventh aspect of the invention provides a sleeve for a catheter comprising a tube having a lumen therethrough, said tube comprising a first, inner layer constructed from fluorinated ethylene propylene (FEP) and a second, outer layer constructed from polyurethane.

Use of FEP is advantageous as FEP provides a very high dielectric strength and consequently a high resistance value. FEP is also very low friction which will allow for a feeding tube to move within the sleeve with little or no resistance. FEP is also optically transparent. This combination of features enables a multi-functional sleeve for use in a catheter to be produced.

BRIEF DESCRIPTION OF THE FIGURES

Specific embodiments of the present invention will now be described, by way of example only, with reference to the accompanying drawings in which.

DETAILED SUMMARY OF THE INVENTION

Figure 1:
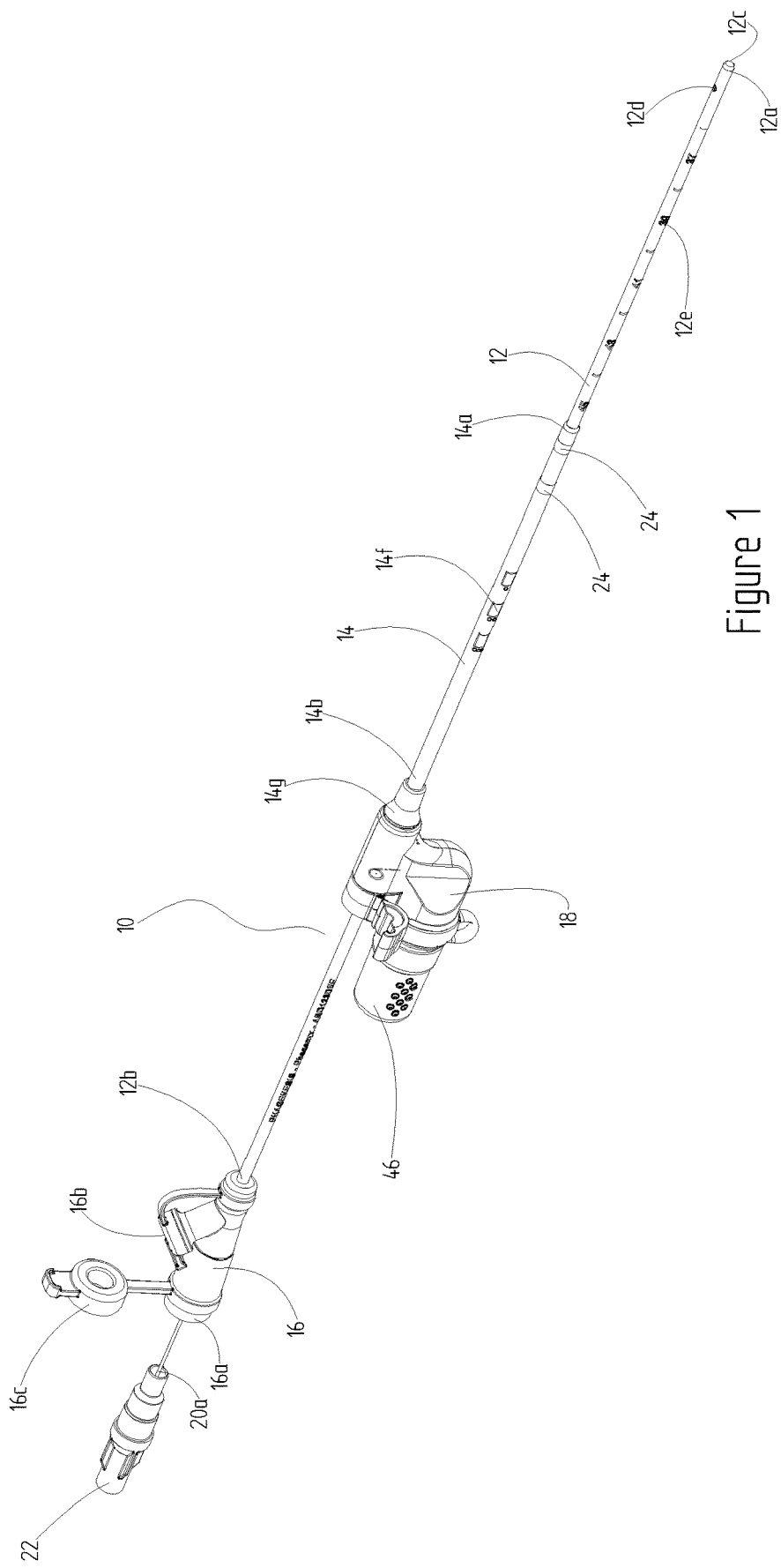
FIG. 1 illustrates an isometric view of a catheter according to embodiments of the present invention.

FIG. 1 shows a catheter 10 in accordance with a preferred embodiment of the invention that is suitable for providing intraluminal electrical pharyngeal neuromuscular stimulation to a patient suffering from dysphagia.

The catheter 10 comprises a feeding tube 12 formed from polyurethane, or other highly flexible material, and a fluorinated ethylene propylene and polyurethane sleeve 14. The catheter 10 is suitably sized for nasal insertion into a patient. The feeding tube 12 of the catheter 10 is of a length sufficient to enable an end to pass through the nose or mouth of the patient, and, via the pharynx and oesophagus, into the stomach of the patient.

The feeding tube 12 of the catheter 10 has a distal end 12a and a proximal end 12b. The proximal end 12b of the feeding tube 12 is restrained by a Y-shaped connector 16 for introducing nutrients into the stomach via the feeding tube 12. The distal end 12a of the feeding tube 12 is unrestrained. The sleeve 14 of the catheter 10 has a distal end 14a and a proximal end 14b. The proximal end 14a of the sleeve is restrained by an S-shaped connector 18 for providing an electrical interface between the catheter 10 and a base station (not shown). The distal end 14b of the sleeve 14 is unrestrained. The feeding tube 12 and sleeve 14 are arranged co-axially with the sleeve 14 surrounding the feeding tube 12.

The feeding tube 12 comprises a rounded tip 12c at its distal end 12b for patient comfort and ease of insertion into the patient. Nutrients are dispersed from the tube 12 via one or more apertures 12d in the circumferential wall of the feeding tube 12 at the distal end 12a thereof and through the distal end 12a of the feeding tube 12 which is open ended. The feeding tube 12 is provided with a plurality of visual indicators 12e along its length, which, in conjunction with the sleeve 14, provide a means of making adjustments of the sleeve 14 relative to the feeding tube 12 taking into account anatomical measurement made on a patient. The feeding tube 12 may be printed with a 1 cm distance guide.

The polyurethane feeding tube material contains 20% barium sulphate to make the tube 12 opaque under X-ray.

The connector 16 is of a Y-shaped construction with a lumen therethrough. One end of the connector 16 receives the proximal end 12b of the feeding tube 12. The other end of the connector 16 provides a primary port 16a which allows connection to an enteral feeding set (not shown). A secondary port 16b on the Y-portion of the container allows connection to a syringe. The secondary port 16b is closable by a cap 16c hingedly connected to the body of the connector 16.

The primary port 16a of the connector 16 also receives a guidewire 20 to assist with inserting the catheter 10 into the patient. The guidewire 20 is formed from stainless steel and is of cable twist construction. The guidewire has a proximal end 20a and a distal end (not shown). The proximal end 20A is received by a guidewire grip 22. The distal end is unrestrained and terminated by a bead. The guidewire grip 22 is a moulded component with a lumen therethrough to receive the guidewire.

The proximal end 14b of the sleeve 14, which is restrained by the housing 18, is surrounded by a strain relief element 14g to reduce strain on the sleeve 14 at an interface between the sleeve 14 and the connector 18.

Figure 2:
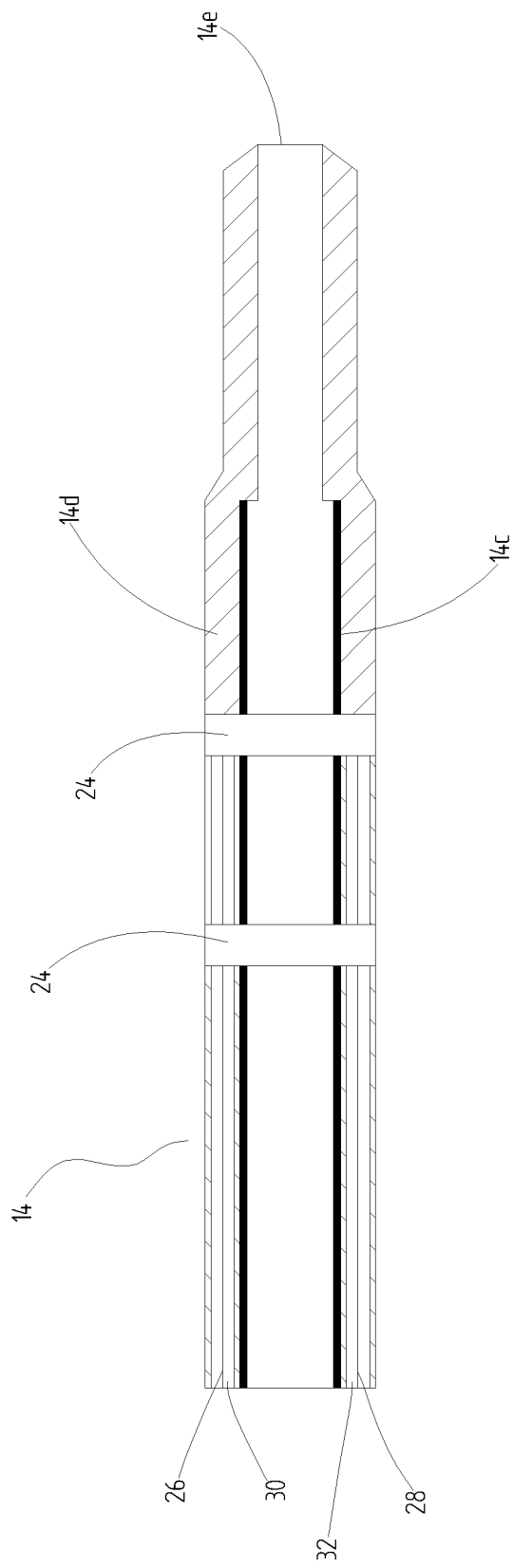
FIG. 2 illustrates a sleeve according to the third and sixth aspects of the present invention.

With reference to FIG. 2, the sleeve 14 is constructed from two distinct layers 14c, 14d. The first, inner layer 14c is formed from fluorinated ethylene propylene and the second, outer layer 14d is formed from polyurethane. A lumen 14e runs longitudinally through the centre of the sleeve 14 to receive the feeding tube 12. A pair of ring electrodes 24 is crimped to the external wall of the sleeve 14. The electrodes 24 are approximately three millimetres wide, positioned approximately ten millimetres apart and are formed from medical grade stainless steel or platinum. Two wires 26, 28 extend from the electrodes and are received in lumens 30, 32 in the outer 14d, polyurethane layer of the sleeve 14. The wires 26, 28 are connected to the connector 18 which provides the electrical interface between the catheter 10 and the base station.

Figure 8:
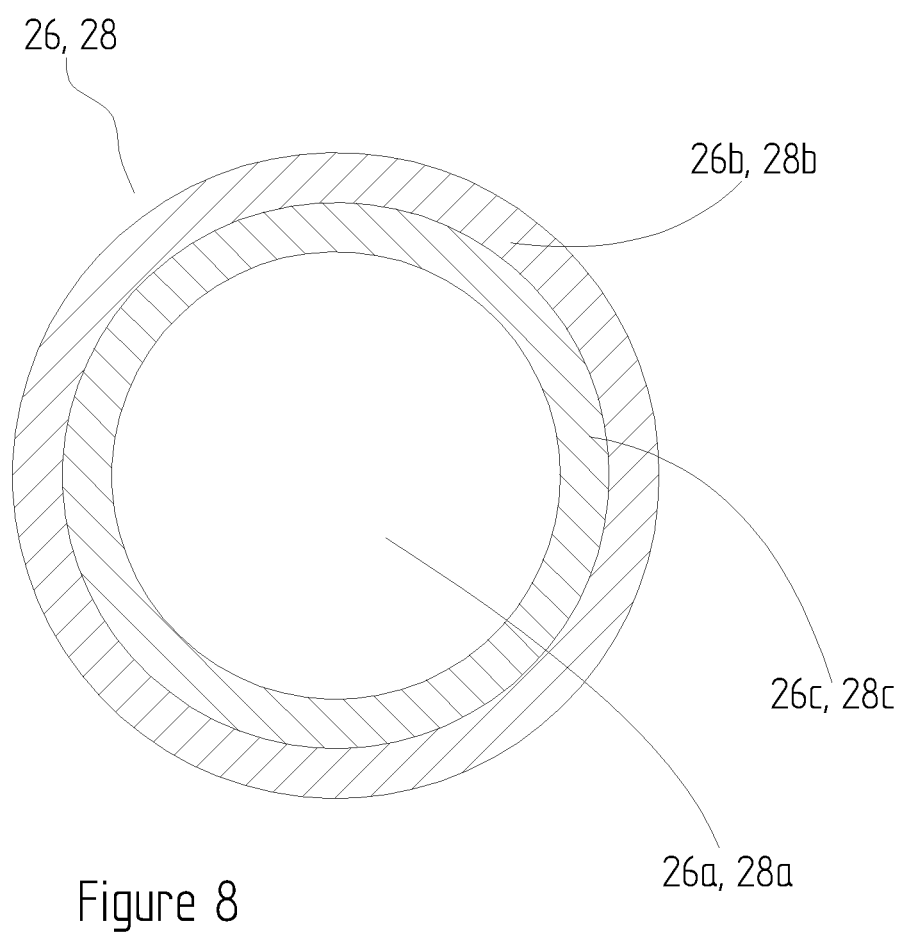
FIG. 8 is a diagram of the structure of a wire according to the fifth aspect of the invention.

The wires 26, 28 each comprise a single strand 26a, 28a, or cable, encapsulated by two distinct types of insulation, as shown in FIG. 8.

A basic insulation 26b, 28b comprises polyurethane, having a dielectric strength of the order of 20 kV/mm, and fluorinated ethylene propylene, having a dielectric strength of the order of 60 kV/mm. The polyurethane part of the basic insulation has a minimum thickness of 0.075 mm and the FEP part of the basic insulation has a minimum thickness of 0.038 mm. In combination, the polyurethane and FEP parts of the basic insulation provide insulation of at least 1500V.

A supplementary insulation 26c, 28c comprises a layer of enamel, having a dielectric strength between 170 and 230 kV/mm, and a layer of parylene, having a dielectric strength of the order of 200 kV/mm. The enamel layer has a thickness of between 0.01 mm to 0.014 mm and the parylene layer has a thickness of between 0.01 mm to 0.02 mm. In combination the enamel and parylene layers of the supplementary insulation provide insulation of between 3700V to 7080V.

The supplementary insulation is applied to the single strand, or cable using vapour deposition in two stages. The enamel is applied directly to the single strand, or cable, and the parylene is applied to the enamel layer. The desired thickness is achieved as a function of time against vapour deposition material density in a chamber. The basic insulation is applied to the supplementary insulation.

The outer 14d polyurethane layer of the sleeve has a thickness which makes up around 88-92% of the wall thickness of the sleeve 14. The inner 14c layer of the sleeve has a thickness which makes up around 8 to 12% of the wall thickness of the sleeve 14. The outer layer 14d of the sleeve extends further towards the distal end 14a of the sleeve 14 than the inner layer 14c of the sleeve 14. The extreme distal end of the outer layer 14e forms a flexible tip.

The outer 14d, polyurethane layer of the sleeve 14 is provided with three guide windows, or rings, 14f (see FIG. 1) which are marked with one, two or three dots, or other visual marks, to signify patients of differing height or other anatomical characteristic. The guide windows 14f are used in conjunction with the visual indicators of the feeding tube 12 to position the sleeve 14 relative to the feeding tube 12 according to a patient's anatomy before the catheter is inserted into the patient.

Figure 3:
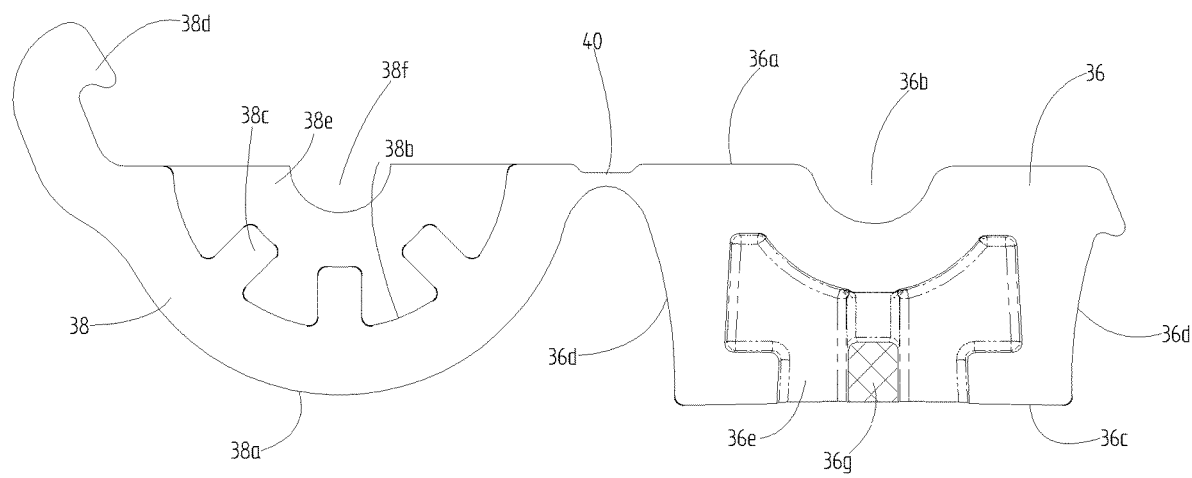
FIG. 3 shows a section through a retaining clip for locking together a feeding tube and a sleeve according to the first aspect of the invention.
Figure 4:
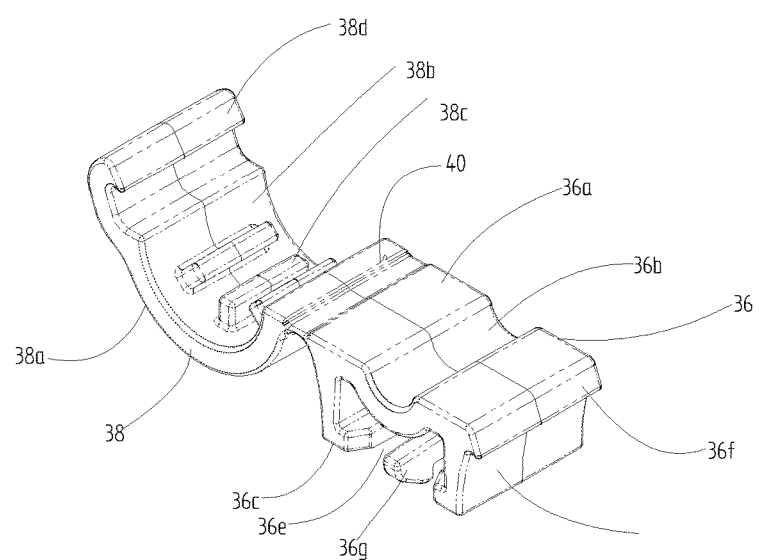
FIG. 4 shows an isometric view of the retaining clip of FIG. 1.

The longitudinal position of the sleeve 14 relative to the feeding tube 12 is restrainable by way of a retaining clip 34 as illustrated in FIGS. 3 and 4. The retaining clip 34 comprises a first part 36 and a second part 38 connected together by way of a living hinge 40. The living hinge is intended to take its normal meaning in the art. The retaining clip 34 is manufactured from polypropylene.

The first part 36 of the retaining clip 34, when viewed in cross section, has a flat top surface 36a with a semi-circular cut-out 36b therethrough for receiving a part of the feeding tube 12. A bottom surface 36c is arranged parallel to the top surface 36a. The bottom surface 36c is connected to the top surface by a pair of curved sidewalls 36d extending upwardly and outwardly from the edges of the bottom surface 36c to the edges of the top surface 36a. The sidewalls 36d each form a substantially L-shape, as viewed in cross-section, by virtue of a recess 36e in the first part 36 of the retaining clip 34. The recess 36e permits the retaining clip 34 to slide on to a mounting formation (not shown) with lateral movement constrained by the L-shape of the sidewalls 36d. A resilient finger 36g on the first part 36 of the retaining clip 34 engages with a recess in the connector 18 to restrain longitudinal movement of the retaining clip 34 relative to the connector 18. The sidewall 36d positioned furthest away from the living hinge 40 is provided with a ridge 36f to, when the retaining clip 34 is closed, hold the first 36 and second 38 parts of the retaining clip 34 in engagement with the feeding tube 12.

The second part 38 of the retaining clip 34 has a curved top wall 38a spaced apart from a curved bottom wall 38b. One end of the curved top wall 38a is joined to the living hinge 40. The curved bottom wall 38b defines a plurality of ribs 38c extending outwardly. The end of the curved bottom wall 38b opposite the living hinge 40 is provided with a spring clip 38d which is co-operable, when the retaining clip 34 is closed, with the ridge 36f of the first part 36 of the retaining clip 34.

In a preferred embodiment, the plurality of ribs 38c are covered by an elastomer insert 38e insertable into the second part 38 of the retaining clip 34. The insert 38e is deformable and comprises a channel 38f which engages against the sleeve 14 when the retaining clip 34 is closed. The high co-efficient of friction of the elastomer insert 38e inhibits longitudinal movement of the sleeve 14 relative to the retaining clip 34 and feeding tube 12. The elastomer insert 38e is not shown in FIG. 4.

Figure 5:
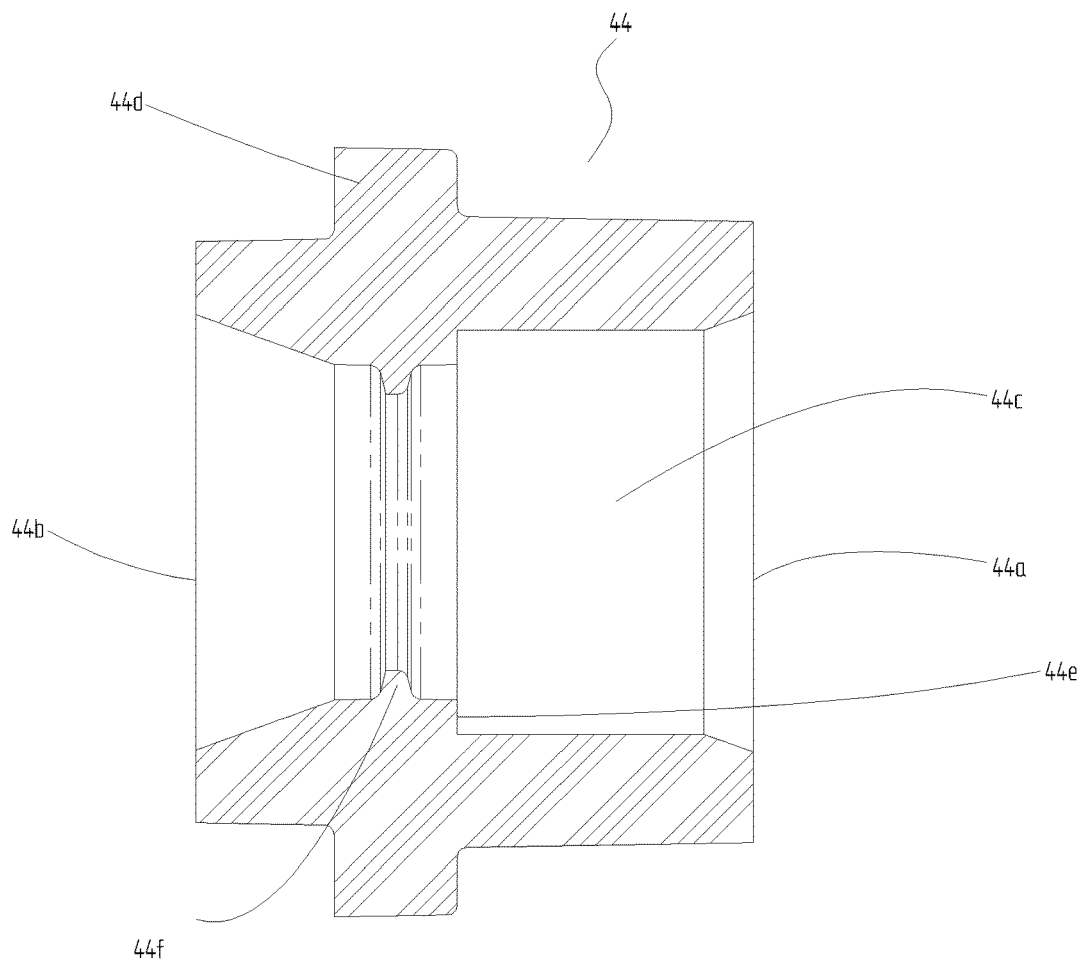
FIG. 5 shows a section through a seal for providing a seal between a feeding tube and a sleeve according to the second aspect of the invention.
Figure 6:
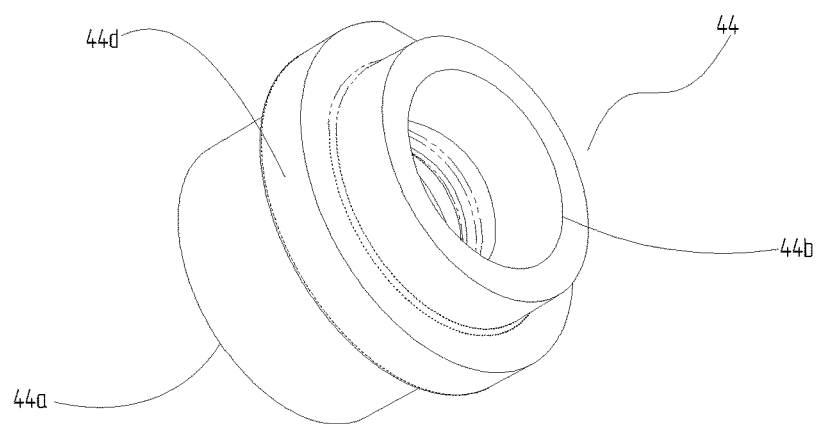
FIG. 6 shows an isometric view of the seal of FIG. 3.

The proximal end of the sleeve 14 is further provided with a cylindrical seal 44, as illustrated in FIGS. 5 and 6, which is bonded to the outer surface of the proximal end 14a of the sleeve 14 at its extreme end. The seal has a first end 44a and a second end 44b with a lumen 44c therebetween. The first end 44a of the seal 44 has a first outer diameter and the second end 44b of the seal 44 has a second outer diameter smaller, than the first. A flange 44d extends from the outer surface of the seal at a position between the first 44a and the second 44b ends thereof. The flange 44d extends around the circumference of the seal 44 and is co-operable with a mounting formation (not shown) within the housing 18 for preventing longitudinal movement of the seal 44, and thus the sleeve 14 within the housing 18.

The first end 44a of the seal 44 has a tapered opening into the lumen 44c. The lumen 44c has a first internal diameter leading from the tapered opening at the first end 44a of the seal 44. The first internal diameter is restricted at a shoulder 44e inside the lumen 44c. The proximal end 14b of the sleeve 14 abuts against the shoulder 44e of the lumen. A second internal diameter of the lumen extends from the shoulder 44e towards the second end 44b of the seal 44.

The second end 44b of the seal 44 has a tapered opening into the lumen 44c. The tapered opening extends to the second internal diameter of the lumen 44c. The second internal diameter has, at its mid-point, a flange 44f extending substantially entirely around its inner circumference. The flange 44f, at its minimum internal diameter, is sized to act against the external surface of the feeding tube thus providing a seal between the sleeve 14 and the feeding tube 12.

In use, the feeding tube 12 is inserted into the second end 44b of the seal 44 and thus into the sleeve 14. The flange 44f within the lumen 44c provides a seal between the outer surface of the feeding tube 12 and the inner surface of the sleeve 14 thus preventing fluid from within a patient being drawn up in a space therebetween by way of capillary action when the sleeve 14 is removed from the patient. The flange 44f also acts to clean any matter off of the feeding tube 12 as it is withdrawn from the patient.

The s-shaped connector 18 is formed from two substantially mirrored parts which are joined by a snap fit connection. The s-shaped connector 18 houses the strain relief element 14g of the sleeve 14, the seal 44 and several electrical components. The housing 18 is formed from medical grade acrylonitrile butadiene styrene. One end of the s-shaped connector 18 receives the proximal end 14a of the sleeve 14 and the other end of the s-shaped connector 18 houses an electrical connector which provides an interface between the catheter 10 and the base station. A protective cap 46 is attached to the s-shaped connector 18 by a lanyard and ring to protect the electrical connector from liquid and dirt. The cap is formed from a thermoplastic elastomer. The s-shaped connector 18 includes a mounting formation (not shown) in the form of rails for mounting the retaining clip 34 to the s-shaped connector 18.

Figure 7:
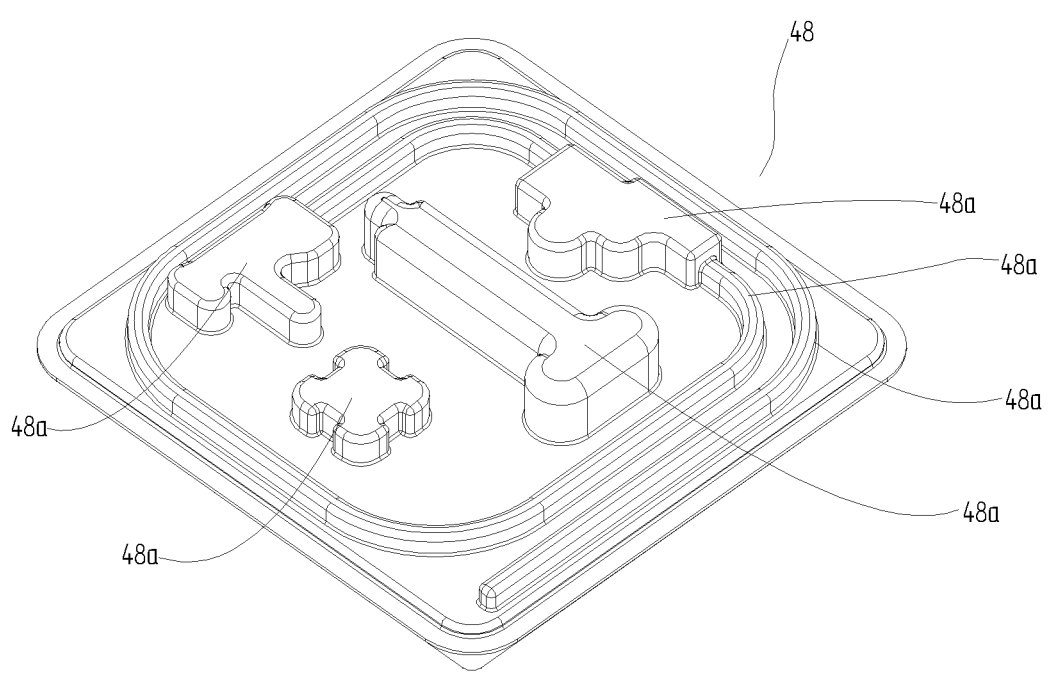
FIG. 7 is an illustration of the packaging for the catheter of FIG. 1 according to the fourth aspect of the invention.

The catheter 10, when assembled, is packed in a storage tray 48, as illustrated in FIG. 7, moulded to receive the specific catheter 10 components. The storage tray 48 comprises a plurality of formations 48a which provide a packaging space corresponding to the desired profile of the feeding tube 12 and/or sleeve 14. When the catheter 10 is packed into the storage tray 48, the feeding tube 12 and/or sleeve 14 take the profile of the packaging space. Once the catheter 10 has been packed into the storage tray 48, the packaged catheter 10 is sterilised by exposing at least a part of the catheter to pre-determined conditions of one or more of temperature, humidity, pressure, vacuum, gas or radiation for a pre-determined time, whereby upon completion of the application of those conditions, at least part of the catheter maintains its deformed shape when removed from the storage container. During exposure, the material of the feeding tube 12 and/or sleeve 14 softens breaking the polymer bonds of the material. When the feeding tube 12 and/or sleeve 14 are removed from exposure to one or more of said conditions, the polymer bonds of the material reform such that at least a part of the feeding tube 12 and/or sleeve 14 naturally take the profile of the packaging space when removed from the storage tray 48.

The shape of the catheter 10 is thus configured to have distinct sections, each having a different radius of curvature. A first section has a first radius of curvature that corresponds to a patient's anatomical transition between the nasal cavity and nasopharynx. A second section has a second radius of curvature that corresponds to a patient's anatomical transition between the nasal cavity and external nares.

The above description is given by way of example only and is not intended to limit the scope of the invention.

What is claimed is:

1. A method of manufacturing a catheter for assisting recovery from dysphagia, the method comprising:
providing a pre-formed storage container having one or more formations for receiving at least part of a catheter;
providing a catheter comprising a feeding tube, a sleeve for receiving the feeding tube and being movable longitudinally relative to the feeding tube and a retaining formation having a first part and a second part connected by a living hinge, attached to the sleeve for fixing the position of the sleeve relative to the feeding tube, the second part being movable relative to the first part between an open position whereby the sleeve can be moved longitudinally relative to the feeding tube and a closed position, whereby the feeding tube is clamped between the first part and the second part to positionally fix the sleeve relative to the feeding tube;

inserting the catheter into the storage container such that at least part of the catheter is received and deformed by the one or more formations of the storage container; and exposing the storage container to pre-determined conditions of one or more of temperature, humidity, pressure, vacuum, gas or radiation for a pre-determined time to both sterilise and shape set the catheter, whereby upon completion of the application of those conditions, the at least part of the catheter maintains its deformed shape when removed from the storage container, wherein the storage container and sterilisation provide conditions to configure the deformed shape of the catheter, wherein the storage container used to confer the shape to the catheter is a final packaging for the catheter.

2. The method of manufacturing a catheter of claim 1, wherein the at least a part of the catheter deformed by the one or more formations of the storage container is the feeding tube and/or the sleeve.

3. The method of manufacturing a catheter of claim 2, wherein deformation occurs by breaking polymer bonds of a material of the feed tube and/or sleeve.

4. The method of manufacturing a catheter of claim 3, wherein when the feeding tube and/or sleeve are removed from exposure to one or more of said conditions, the polymer bonds of the material reform such that at least a part of the feeding tube and/or sleeve naturally take the profile of a packaging of the storage container.

5. The method of manufacturing a catheter of claim 1, where the predetermined conditions that facilitate deformation occur during a terminal sterilisation step of manufacturing.

6. The method of manufacturing according to claim 5, wherein the terminal sterilisation step comprises ethyl oxide sterilisation.

7. A method of manufacturing a catheter for assisting recovery from dysphagia, the method comprising:

providing a pre-formed storage container having one or more formations for receiving at least part of a catheter;

providing a catheter comprising a feeding tube, a sleeve for receiving the feeding tube and being movable longitudinally relative to the feeding tube and a retaining formation having a first part and a second part connected by a living hinge, attached to the sleeve for fixing the position of the sleeve relative to the feeding tube, the second part being movable relative to the first part between an open position whereby the sleeve can be moved longitudinally relative to the feeding tube and a closed position, whereby the feeding tube is clamped between the first part and the second part to positionally fix the sleeve relative to the feeding tube;

inserting the catheter into the storage container such that at least part of the catheter is received and deformed by the one or more formations of the storage container; and with the at least part of the catheter received and deformed by the one or more formations, exposing the storage container to pre-determined conditions of one or more of temperature, humidity, pressure, vacuum, gas or radiation for a pre-determined time to simultaneously sterilise and shape set the catheter, whereby upon completion of the application of those conditions, the at least part of the catheter maintains its deformed shape when removed from the storage container, wherein the storage container used to confer the shape to the catheter is a final packaging for the catheter.

* * * * *